(12) United States Patent
Siess et al.

(10) Patent No.: US 11,690,996 B2
(45) Date of Patent: Jul. 4, 2023

(54) BLOOD PUMP

(71) Applicant: Abiomed Europe Gmbh, Aachen (DE)

(72) Inventors: Thorsten Siess, Aachen (DE); Walid Aboulhosn, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 89 days.

(21) Appl. No.: 17/074,841

(22) Filed: Oct. 20, 2020

(65) Prior Publication Data

US 2021/0038785 A1 Feb. 11, 2021

Related U.S. Application Data

(62) Division of application No. 15/556,646, filed as application No. PCT/EP2016/055646 on Mar. 16, 2016, now Pat. No. 10,842,921.

(30) Foreign Application Priority Data

Mar. 18, 2015 (EP) ..................................... 15159677

(51) Int. Cl.
*A61M 60/00* (2021.01)
*A61M 60/824* (2021.01)
(Continued)

(52) U.S. Cl.
CPC .......... *A61M 60/824* (2021.01); *A61M 60/13* (2021.01); *A61M 60/221* (2021.01);
(Continued)

(58) Field of Classification Search
CPC ........................... A61M 60/818; A61M 60/824
(Continued)

(56) References Cited

U.S. PATENT DOCUMENTS 6,116,862 A 9/2000 Rau et al.
2005/0107657 A1* 5/2005 Carrier ................ F04D 13/0606
600/16

(Continued)

FOREIGN PATENT DOCUMENTS

EP 2662099 A1 11/2013
JP 2010534080 A 11/2010
(Continued)

OTHER PUBLICATIONS

International Search Report and Written Opinion PCT/EP2016/055646, dated Jun. 10, 2016 (10 pages).
(Continued)

*Primary Examiner* — Nicole F Lavert
*Assistant Examiner* — Nicole F Johnson
(74) *Attorney, Agent, or Firm* — Botos Churchill IP Law LLP

(57) ABSTRACT

A blood pump comprises a pump casing having a blood flow inlet and a blood flow outlet connected by a passage, and an impeller arranged in said pump casing so as to be rotatable about an axis of rotation. The impeller is provided with blades sized and shaped for conveying blood along the passage from the blood flow inlet to the blood flow outlet, and is rotatably supported in the pump casing by a first bearing at a first axial end of the impeller and a second bearing axially spaced apart from the first bearing. The first bearing comprises a projection extending along the axis of rotation and connected to one of the impeller and the pump casing and a cavity in the other one of the impeller and the pump casing, the projection comprising an enlarged portion that engages the cavity such that the first bearing and the second bearing are arranged to bear axial forces in the same axial direction.

8 Claims, 14 Drawing Sheets

(51) Int. Cl.
  *A61M 60/221* (2021.01)
  *A61M 60/237* (2021.01)
  *A61M 60/232* (2021.01)
  *A61M 60/422* (2021.01)
  *A61M 60/825* (2021.01)
  *A61M 60/13* (2021.01)
  *A61M 60/148* (2021.01)
  *A61M 60/414* (2021.01)
  *A61M 60/419* (2021.01)

(52) U.S. Cl.
  CPC ........ *A61M 60/232* (2021.01); *A61M 60/237* (2021.01); *A61M 60/422* (2021.01); *A61M 60/825* (2021.01); *A61M 60/148* (2021.01); *A61M 60/414* (2021.01); *A61M 60/419* (2021.01); *A61M 2205/3334* (2013.01)

(58) Field of Classification Search
  USPC .......................................................... 600/16
  See application file for complete search history.

(56) References Cited

U.S. PATENT DOCUMENTS

| | | | |
|---|---|---|---|
| 2008/0262289 A1 | 10/2008 | Goldowsky | |
| 2008/0269880 A1 | 10/2008 | Jarvik | |
| 2009/0118567 A1* | 5/2009 | Siess | F04D 29/406 600/16 |
| 2010/0198147 A1 | 8/2010 | Perovitch | |
| 2013/0331934 A1* | 12/2013 | Kabir | A61F 2/24 623/3.13 |

FOREIGN PATENT DOCUMENTS

| | | |
|---|---|---|
| JP | 2010534081 A | 11/2010 |
| JP | 2013053519 A | 3/2013 |
| JP | 2013053591 A | 3/2013 |
| JP | 2021065585 A | 4/2021 |
| WO | 9500185 A1 | 1/1995 |
| WO | 03075981 A1 | 9/2003 |
| WO | 2009010888 A2 | 1/2009 |
| WO | 2012149946 A1 | 11/2012 |
| WO | 2013185073 A1 | 12/2013 |
| WO | 2014109029 A1 | 7/2014 |

OTHER PUBLICATIONS

Office Action in Chinese Application No. 201680015836.6 dated Jun. 28, 2020 in English (13 pages).
Office Action from Korean Patent Application No. 10-2017-7027678, dated Feb. 8, 2023 (13 pages).
Office Action from corresponding Japanese Application No. 2002-092906 dated Apr. 12, 2023 (7 pp.).

* cited by examiner

BLOOD PUMP

CROSS-REFERENCE TO RELATED APPLICATIONS

This application is a divisional of U.S. patent application Ser. No. 15/556,646, filed Sep. 8, 2017 now U.S. Pat. No. 10,842,921, which is a United States National Stage filing under 35 U.S. C. § 371 of International Application No. PCT/EP2016/055646, filed Mar. 16, 2016, which claims priority from European Patent Application No. 15159677.2, filed Mar. 18, 2015 now European Patent No. 3069739 B1, the contents of all of which are incorporated by reference herein in their entirety. International Application No. PCT/EP2016/055646 was published as WO2016146663A1 under PCT Article 21(2) in English.

BACKGROUND

This invention relates to blood pumps to be implanted in a patient for supporting the patient's heart. In particular, the blood pump may be used as a "bridge to recovery" device, whereby the blood pump temporarily supports the patient's heart until it has sufficiently recovered.

Blood pumps of different types are known, such as axial blood pumps, centrifugal blood pumps or mixed type blood pumps, where the blood flow is caused by both axial and radial forces. Blood pumps may be inserted into a patient's vessel such as the aorta by means of a catheter, or may be placed in the thoracic cavity. A blood pump typically comprises a pump casing having a blood flow inlet and a blood flow outlet connected by a passage. In order to cause a blood flow along the passage from the blood flow inlet to the blood flow outlet an impeller is rotatably supported within the pump casing, with the impeller being provided with blades for conveying blood.

The impeller is supported within the pump casing by means of at least one bearing, which may be of different types depending on the intended use of the blood pump, for instance whether the blood pump is intended only for short term use (some hours or some days) or long term use (weeks or years). A variety of bearings are known, such as contact-type bearings and non-contact bearings. In non-contact bearings the bearing surfaces do not contact each other, e.g. in magnetic bearings, in which the bearing surface "levitate" due to repelling magnetic forces. Generally, contact-type bearings may include all types of bearings, in which the bearing surfaces may contact at least partially during operation of the pump at any time (i.e. always or intermittently), e.g. in slide bearings, pivot bearings, hydrodynamic bearings, hydrostatic bearings, ball bearings etc. or any combination thereof. In particular, contact-type bearings may be "blood immersed bearings", where the bearing surfaces have blood contact. Contact-type bearings, such as pivot bearings, may heat up during use and are subject to mechanical wear. Mechanical wear may be increased by a magnetic coupling between the electric motor of the pump and the impeller for driving the impeller. When the contact-type bearing and the magnetic coupling are disposed at the same axial end of the impeller, mechanical wear of the bearing may increase because the magnetic coupling attracts the impeller, thereby increasing the contact pressure on the bearing surfaces. This may lead to a high load (e.g. 10 Newton) on a small bearing surface (e.g. in a pivot bearing in catheter pump e.g. in the range of 1 mm in diameter).

SUMMARY OF THE INVENTION

It is a primary object of the present invention to provide a blood pump having an impeller that is supported in a pump casing by means of a bearing, wherein mechanical wear of the bearing can be reduced. In particular, it is another object of the present invention to relieve a bearing in a blood pump from excessive loading.

The primary object is achieved according to the present invention by a blood pump with the features of independent claim 1. Preferred embodiments and further developments of the invention are specified in the claims dependent thereon.

Like known blood pumps, the blood pump according to the invention comprises a pump casing having a blood flow inlet and a blood flow outlet connected by a passage. An impeller or rotor is arranged in said pump casing so as to be rotatable about an axis of rotation, which may be the longitudinal axis of the impeller, with the impeller being provided with blades sized and shaped for conveying blood along the passage from the blood flow inlet to the blood flow outlet. The impeller is rotatably supported in the pump casing by a first bearing at a first axial end of the impeller and a second bearing axially spaced apart from the first bearing.

According to the invention, the first bearing comprises a projection extending along the axis of rotation and connected to one of the impeller and the pump casing and a cavity in the other one of the impeller and the pump casing. The term "cavity" may comprise any kind of cavity, hollow space, recess, opening, or bore. The projection comprises an enlarged portion that engages the cavity such that the first and second bearings are arranged to bear axial forces in the same axial direction. For instance, the enlarged portion may be supported by or enclosed in the cavity. In other words, the first bearing relieves the second bearing by carrying at least part of the axial force that acts on the bearing surfaces of the second bearing. Since both bearings support the impeller in the same "bearing direction", the load on each of the bearings can be reduced. They "share" the load. This is achieved by providing simple mechanical means in the form of a projection with an enlarged portion and a corresponding cavity such that the impeller is to a certain extent "suspended" by the first bearing. Preferably, the projection and the enlarged portion are comprised in the impeller, with the cavity being static and part of the pump casing. The cavity may be disposed in a supporting structure of the pump casing. It will be appreciated, however, that the arrangement may be vice versa without affecting the functionality.

Preferably, the cavity corresponds in size and shape to the enlarged portion. This may improve the bearing characteristics because a displacement of the impeller in an axial direction or radial direction or both can be reduced or avoided if the cavity and the enlarged portion are adapted to each other in size and shape. In particular, the first bearing can be arranged to bear axial forces in two opposed axial directions. However, it is not necessary that the cavity corresponds in size and shape to the enlarged portion as long as the first bearing can bear axial forces in the same axial direction as the second bearing. For instance, in an opposite axial direction, i.e. the direction away from the second bearing, the cavity may be open or may at least provide enough space such that a movement of the impeller in this direction is possible.

Preferably, the enlarged portion is at least partially spherical in shape. For example, the enlarged portion may be a spherical cap. Accordingly, the cavity may be at least partially spherical as well. However, the enlarged portion may have any shape that is suitable for achieving the inventive concept. In particular, any shape that is rotationally symmetrical and has a ledge to bear axial forces may be suitable for the first bearing. The enlarged portion may be e.g. cylindrical or conical. The enlarged portion may be snap fitted into the cavity, which is a simple way to mount the first bearing. The material of the enlarged portion or the cavity or both may have sufficient resilient properties to allow a snap fit connection. In another embodiment the cavity or the enlarged portion may be formed by molding over a preexisting part that is made for example from a metallic or ceramic material or alike and allow the shrinkage of the molded plastic to create a dynamic joint.

In an embodiment, the second bearing may be a contact-type bearing comprising a bearing surface of the impeller facing a bearing surface of the pump casing, preferably a pivot bearing. A pivot bearing allows for rotational movement as well as pivoting movement to some degree.

The blood pump may further comprise a shaft extending along and rotatable about the axis of rotation and having the impeller mounted thereon, the shaft having a first end portion forming part of the first bearing and a second end portion forming part of the second bearing. In particular, the first end portion of the shaft may comprise the enlarged portion, such as a spherical cap. The shaft may have an outer diameter that is substantially equal to an outer diameter of the enlarged portion, with the projection forming a neck arranged between the shaft and the enlarged portion. This allows a compact arrangement and is advantageous for the snap fit connection. The second end portion of the shaft may comprise a bearing surface of the second bearing, said bearing surface being concave, e.g. spherical, for instance forming part of a pivot bearing. It will be appreciated that the shaft may be separately formed or integrally formed with the impeller. It will be further appreciated that parts of the shaft are in direct blood contact for purpose of improved heat transfer to the surrounding blood. The shaft is preferably made of a heat conducting material (metal, silicon carbide, or similar material) so the heat generated within the portion of the bearing can be well transferred to the surrounding blood in order to limit the temperature to 55° C. or less.

In an embodiment, a wall of the cavity may comprise at least two sections separated by a gap, for example two, three or four sections. The gap may be in fluid connection with the passage to allow blood to enter the cavity. This enables the first bearing to be washed out by blood flowing through the blood pump or by any other rinsing fluid.

In an embodiment, the enlarged portion of the first bearing may comprise at least one magnet, and the pump casing, preferably the cavity, may also comprise at least one magnet. The magnets may be arranged such that a repelling magnetic force pointing in an axial direction away from the second bearing is caused. This arrangement allows for relieving the second bearing because the magnetic force of the first bearing pulls the impeller in a direction away from the second bearing. Apart from that, due to the design of the first bearing as a magnetic bearing, mechanical wear of the first bearing in an axial direction can be avoided.

In an embodiment, at least one of the bearing surfaces of at least one of the first and second bearings may be supported by at least one spring, wherein the at least one spring is arranged to bear axial forces in an axial direction from the second bearing towards the first bearing. Specifically, the second bearing can be relieved by providing at least one spring that receives and dampens part of the load that acts on the bearing surfaces of the second bearing. At least one spring may be disposed on a side of the second bearing facing away from the first bearing. For instance, at least one spring may be disposed in a portion of the casing supporting a static bearing surface of the second bearing. The spring force may be chosen to be less than the load on the second bearing. In this case, the load on the second bearing is limited to the amount of the spring force, while the remainder of the load is supported by the first bearing. Alternatively or in addition, the first bearing may be spring supported by at least one spring, in particular the portion of the pump casing comprising the cavity, whereby the spring causes a force in an axial direction away from the second bearing It will appreciated that the spring can be composed of a metallic material or may be formed out of a polymeric material for example in the shape of a O-ring or similar shape that serves the same function as a coil metallic spring. In an embodiment, at least one of the bearing surfaces of second bearing may be supported by a flexible structure that may have a known force when flexed.

Further means for relieving the second bearing can be provided. For instance, repelling magnets could be provided in or near, e.g. around, the bearing surfaces of the second bearing. In order to reduce or eliminate axial forces caused by the attracting magnetic forces that transmit rotation to the impeller, the magnetic drive arrangement may be disposed in a radial direction, where the magnetic drive is circumferentially arranged around the impeller. Likewise, in an arrangement in which the magnetic drive is disposed in an axial direction with respect to the impeller, the magnetic flux may be deflected such that it acts on the impeller in a radial direction. Further, alternatively or additionally, a supporting bearing may be provided that carries part of the load of the second bearing. The supporting bearing may be a ball bearing that comprises a plurality of balls running between a surface of the impeller and a surface of the housing, preferably in respectively aligned grooves, surrounding the second bearing.

It will be appreciated that according to the invention two mechanical bearing are employed to center the impeller. The spatial distribution of both bearings along the axis of rotation allows for a stiff bearing/impeller arrangement. The later allows for pulsatile pump operation where the impeller may transfer from below critical speeds with every heart cycle. Due to the stiff arrangement provided by the two mechanical bearings, vibration of the impeller during critical speeds can be reduced. The pulsatile and synchronized pump operation with the heart is considered to be highly advantageous to achieve heart recovery. In addition it will be appreciated that mechanical bearings are employed because of their small size, which is mandated by any small sized pump intended to be placed inside a patient's vessel.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
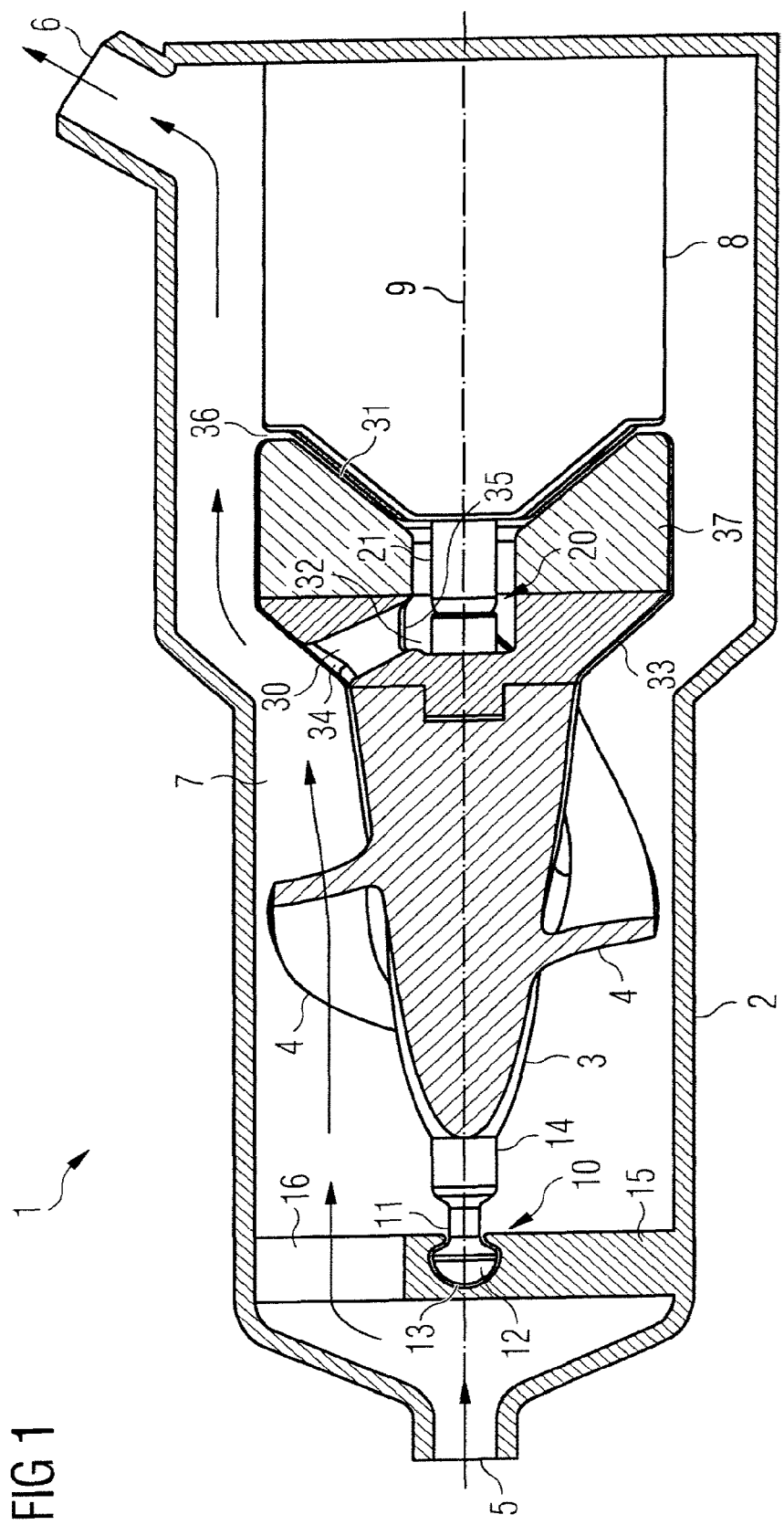
FIG. 1 shows a cross sectional view of a blood pump according to the invention.

Referring to FIG. 1, a cross sectional view of a blood pump 1 is illustrated. The blood pump 1 is designed for extracorporeal, extracardiac or extraluminal use and comprises a pump casing 2 with a blood flow inlet 5 and a blood flow outlet 6. During operation, the pump casing 2 is placed outside a patient's body and the blood flow inlet 5 and the blood flow outlet 6 are connected to respective connectors (in particular inflow from the heart and outflow to the aorta). The blood is conveyed along a passage 7 connecting the blood flow inlet 5 and the blood flow outlet 6. An impeller 3 having a shaft 14 is provided for conveying blood along the passage 7 and is rotatably mounted about an axis of rotation 9 within the pump casing 2 by means of a first bearing 10 and a second bearing 20. The axis of rotation 9 is preferably the longitudinal axis of the impeller 3. Both bearings 10, 20 are contact-type bearings as will be described in more detail below. The second bearing 20 is a pivot bearing having spherical bearing surfaces that allow for rotational movement as well as pivoting movement to some degree. The first bearing 10 is disposed in a supporting member 15 to stabilize the rotation of the impeller 3, the supporting member 15 having at least one opening 16 for the blood flow. Blades 4 are provided on the impeller 3 for conveying blood once the impeller 3 rotates. Rotation of the impeller 3 is caused by an electric motor 8 magnetically coupled to an end portion 37 of the impeller 3. Other suitable driving mechanisms are possible as will be appreciated by a person skilled in the art. The illustrated blood pump 1 is a mixed-type blood pump, wherein the major direction of flow is axial. It will be appreciated that the blood pump 1 could also be a purely axial blood pump, depending on the arrangement of the impeller 3, in particular the blades 4.

The impeller 3 comprises a portion 33 that extends radially outwards. The portion 33 can be denoted as a yoke, flange portion or end portion. At least one wash out channel 30, preferably two or more, such as three, four, five or six wash out channels 30, only one of which is shown in FIG. 1, extends through the impeller 3, in particular through the portion 33, so as to allow for washing out or rinsing a clearance 31 between the impeller 3 and a static part of the blood pump 1, in particular the pump casing 2 or the motor 8, which may be regarded as associated with the pump casing 2. The at least one wash out channel 30 may also extend at least partially into the main portion of the impeller 3 beyond the portion 33. The wash out channel 30 has a first opening 34 and a second opening 35. The first opening 34 forms a fluid connection between the passage 7 and the wash out channel 30, while the second opening 35 is in fluid connection with the clearance 31. In particular, the second opening 35 is in fluid connection with a central bore or central opening 32 of the portion 33 accommodating the second bearing 20, such that the second bearing 20 can be washed out and cooled.

Figure 6:
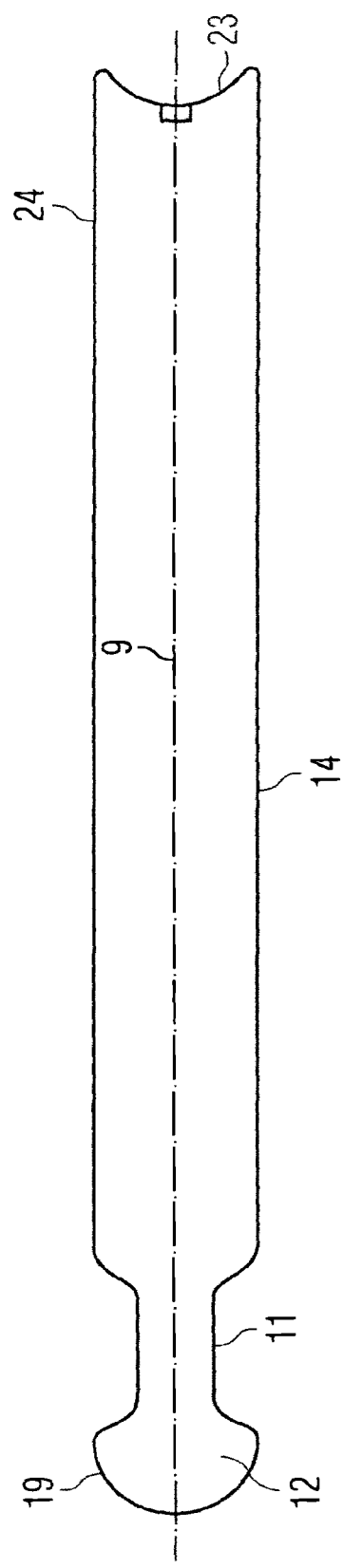
FIG. 6 shows a cross sectional view of a first shaft of the blood pump.
Figure 7:
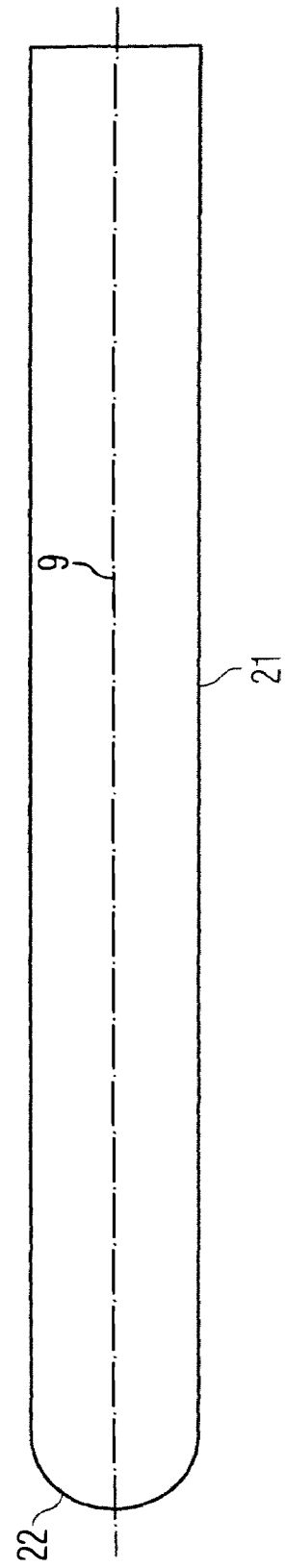
FIG. 7 shows a cross sectional view of a second shaft of the blood pump.

The second bearing 20 comprises a first bearing surface 23 disposed at a second end portion 24 of the first shaft 14 (see FIG. 6) and a second bearing surface 22 at an end portion of a second shaft 21, in particular in a recess at the center of a second shaft 21 (see FIG. 7). Both bearings surfaces 22, 23 are preferably spherical. Due to the magnetic coupling between the electric motor 8 and the end portion 37, the impeller 3 is attracted towards the motor 8 which increases the pressure between the bearing surfaces 22, 23 of the second bearing 20. In order to relieve the second bearing 20, the first bearing 10 is arranged at the opposed axial end portion 19 of the first shaft 14 and is arranged to bear axial loads in the same axial direction as the second bearing 20.

The first bearing 10 includes an enlarged portion 12 that engages a cavity 13 in the pump casing 2, in particular in the supporting structure 15, which may be regarded as part of the pump casing 2. In particular, the enlarged portion 12 may be supported by, enclosed in, or entrapped in the cavity 13. The enlarged portion 12 may be snap fitted into the cavity 13 or otherwise mounted. More specifically, the first bearing 10 includes a protrusion 11 extending axially at the first end portion 19 of the shaft 14 including the enlarged portion 12. In the embodiments shown, the enlarged portion 12 is formed as a cap that is partially spherical in shape. However, any rotationally symmetric shape may be chosen for the enlarged portion 12 that is suitable for bearing axial loads in the same direction as the second bearing 20. The projection 11 forms a neck having a smaller diameter than the enlarged portion 12. As shown in FIG. 6, the enlarged portion 12 has the same diameter as the shaft 14. The diameters of the enlarged portion 12 and the shaft 14 could be different. In particular, the diameter of the enlarged portion 12 could be smaller or greater than the diameter of the shaft 14. The neck also may be omitted. The shaft 14 may also be integrally formed with the impeller 3.

Figure 2:
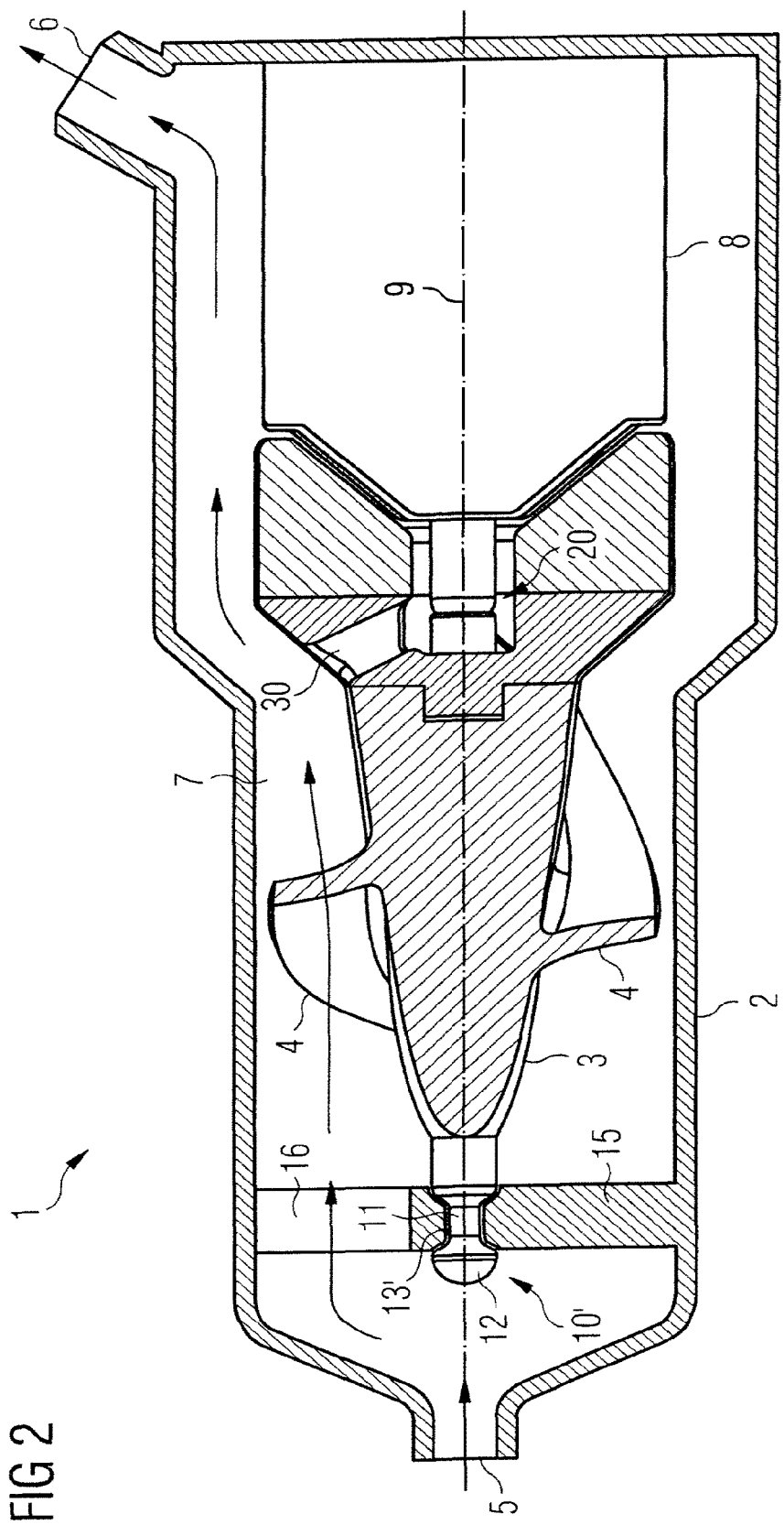
FIG. 2 shows a cross sectional view of a blood pump according to another embodiment.
Figure 3:
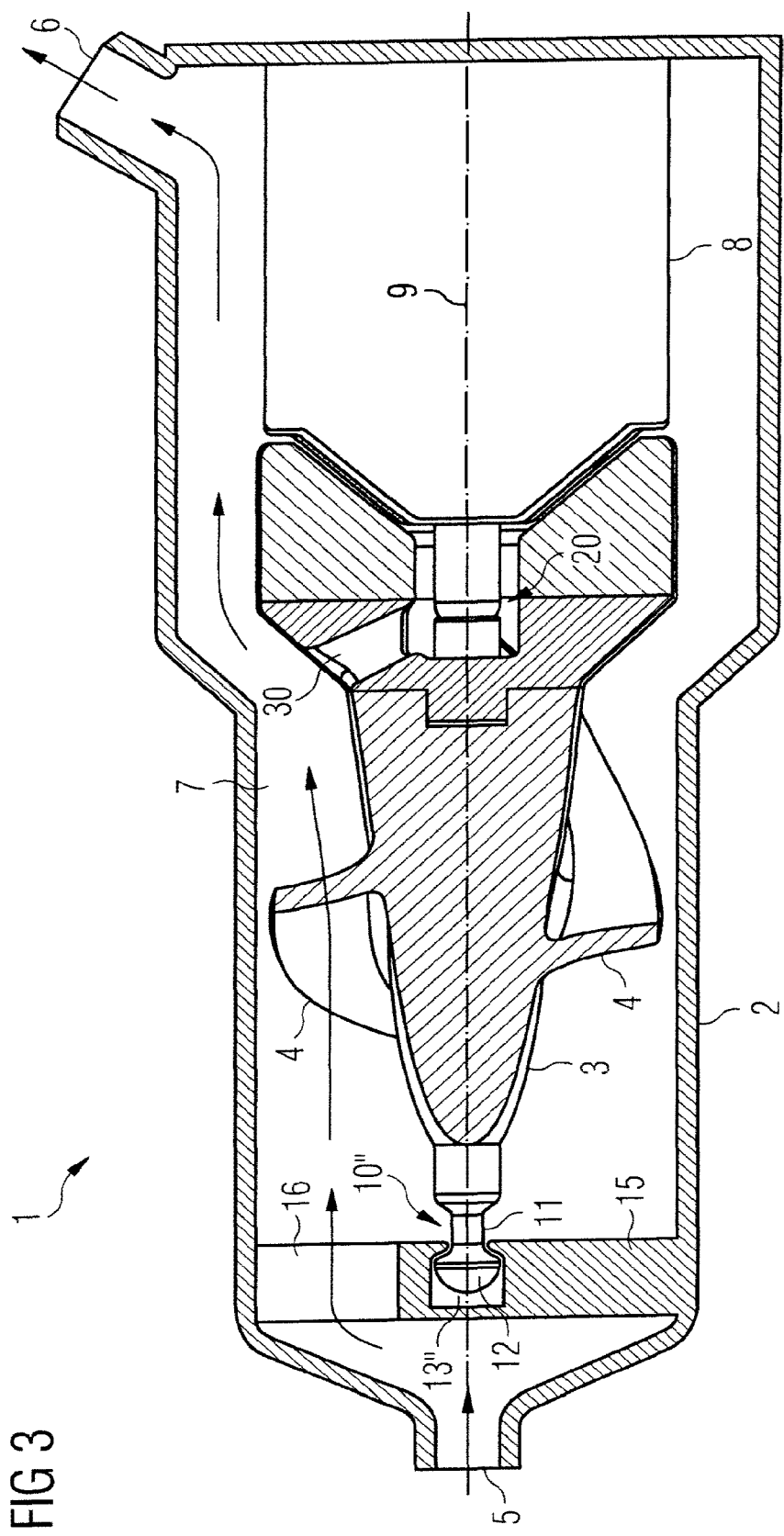
FIG. 3 shows a cross sectional view of a blood pump according to still another embodiment.

In the embodiment of FIG. 1, the cavity 13 substantially corresponds in size and shape to the enlarged portion 12. Therefore, the first bearing 10 does not only bear loads in the same axial direction as the second bearing 20 but supports the impeller 3 in both axial directions. In the embodiment of FIG. 2, the cavity 13' is open to a side that faces away from the second bearing 20. However, the supporting structure 15 is sized and shaped to correspond to the size and shape of the neck 11, such that the impeller 3 is supported in both axial as well as radial directions. It will be appreciated that the supporting structure 15 may be smaller to allow some axial movement in a direction away from the second bearing 20. In the embodiment of FIG. 3, the impeller 3 may move in an axial direction away from the second bearing 20, which may occur due to the rotating movement of the impeller 3 in the blood flow. In this embodiment, the cavity 13" is axially enlarged in a direction away from the second bearing 20.

Figure 4A:
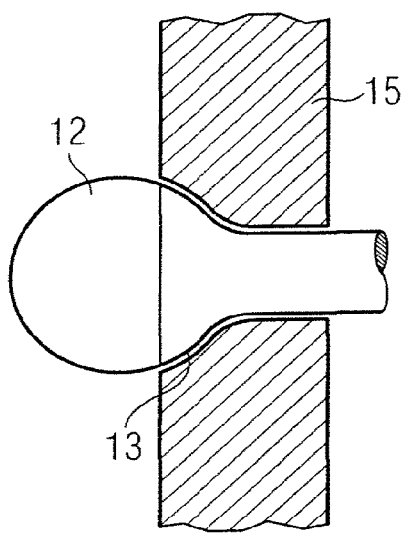
FIGS. 4A-4D show different embodiments of the first bearing.
Figure 4B:
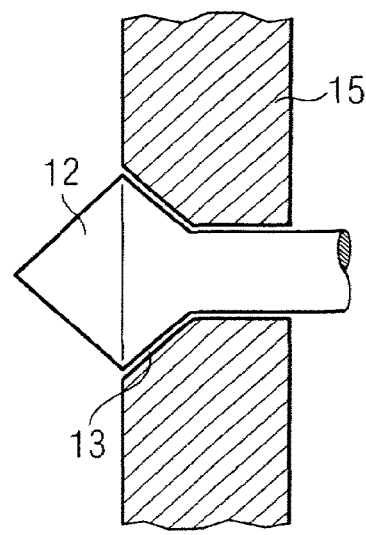
Figure 4C:
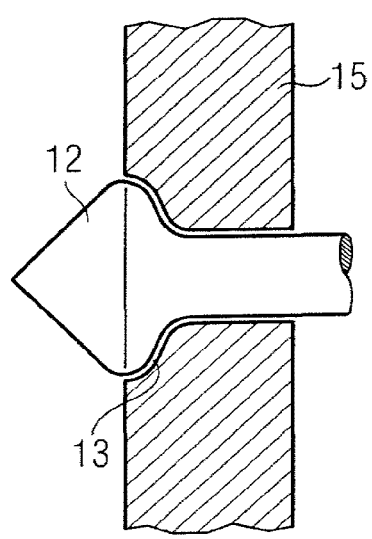
Figure 4D:
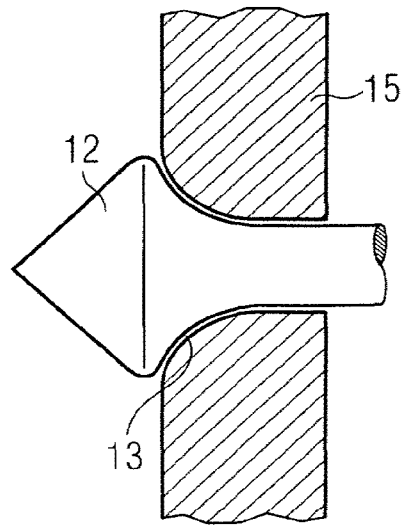

FIGS. 4A-4D show different embodiments of the first bearing 10, in particular the enlarged portion 12 and the cavity 13. In FIG. 4A the enlarged portion is substantially spherical similar to the enlarged portion shown in FIGS. 1 to 3. The section that contacts the cavity 13 in the supporting structure 15 may have a different diameter than the remaining section of the enlarged portion 12 and may be convex. Alternatively, this section may be concave. In the embodiment of FIG. 4B the enlarged portion 12 is conical or diamond shaped. FIGS. 4C and 4D show similar embodiments, wherein the enlarged portion 12 has a conical or tapered section. This facilitates assembly of the bearing 10. In FIG. 4C, the section of the enlarged portion 12 that contacts the cavity 3 in the supporting structure 15 is spherical and convex, whereas it is concave in FIG. 4D. It will be appreciated that any rotationally symmetrical shape may be used for the enlarged portion 12.

Figure 5:
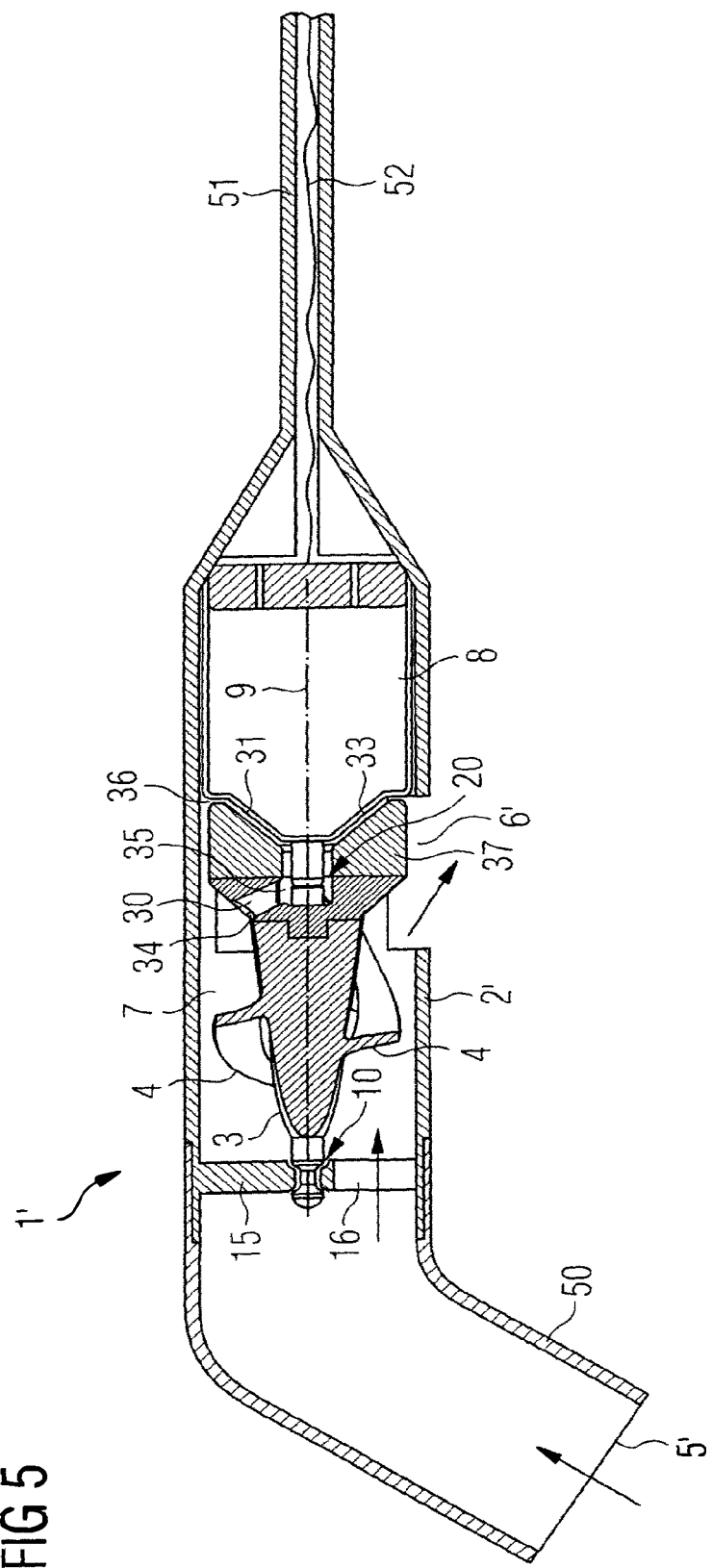
FIG. 5 shows a cross sectional view of a blood pump according to an embodiment, in which the blood pump is designed as a catheter pump.

Referring now to FIG. 5, an embodiment is shown that is similar to the aforementioned embodiment of FIGS. 1 to 3, in particular to that of FIG. 2, with the difference that it is designed as a catheter pump 1'. The blood flow inlet 5' is at the end of a flexible cannula 50 which is placed through a heart valve, such as the aortic valve, during use, while the blood flow outlet 6' is placed in a side of the pump casing 2' and is placed in a heart vessel, such as the aorta. The blood pump V is connected to a catheter 51, and an electric wire 52 extends through the catheter 51 for driving the pump 1'. Both blood pumps 1 and V function in the same way. It will be appreciated that all features described are applicable for both extracorporeal pumps and catheter pumps.

Figure 8:
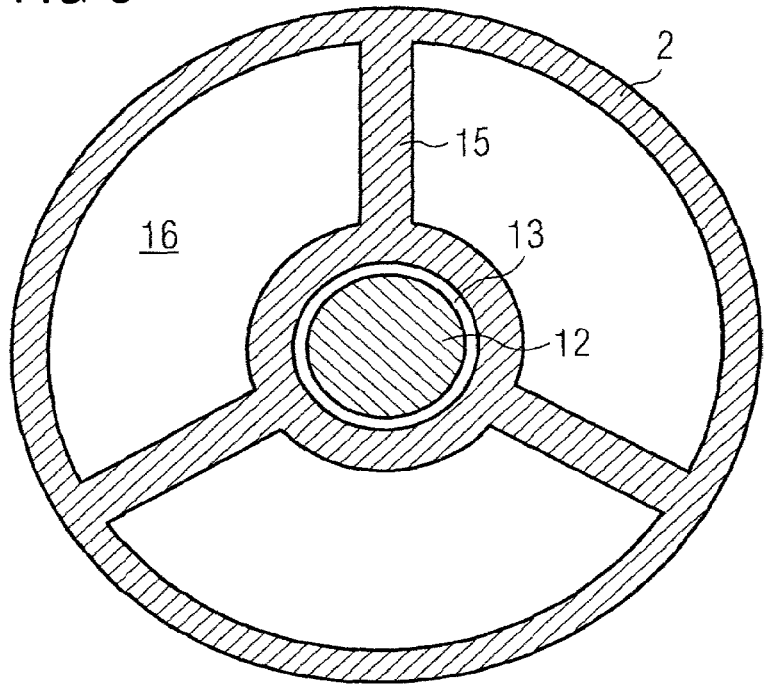
FIG. 8 shows a cross sectional view of a supporting structure for the first shaft.
Figure 9A:
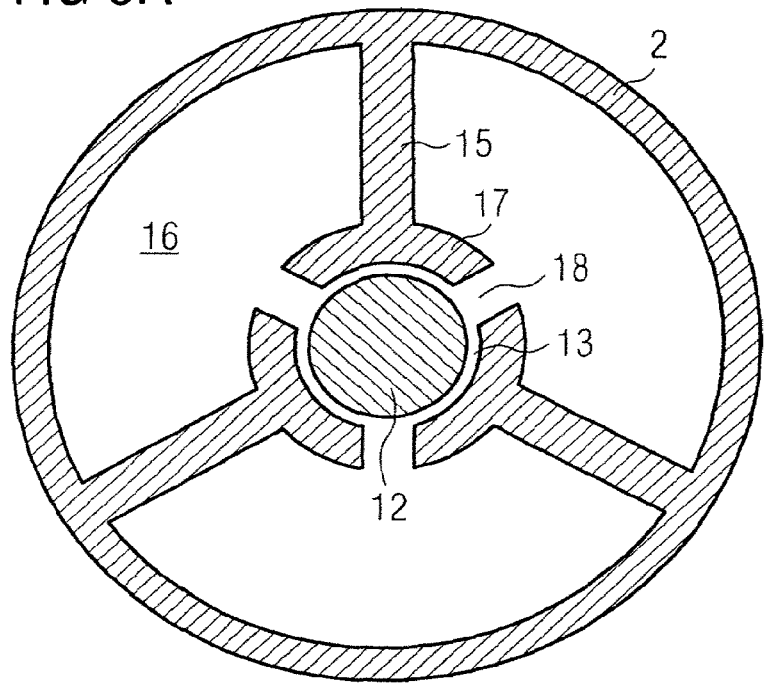
FIGS. 9A-9C show cross sectional views of a supporting structure for the first shaft according to other embodiments.
Figure 9B:
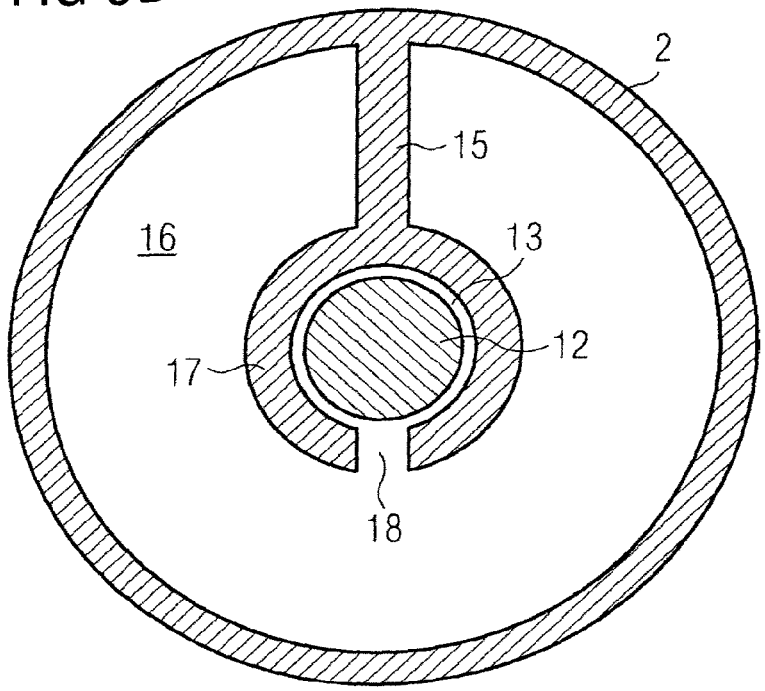
Figure 9C:
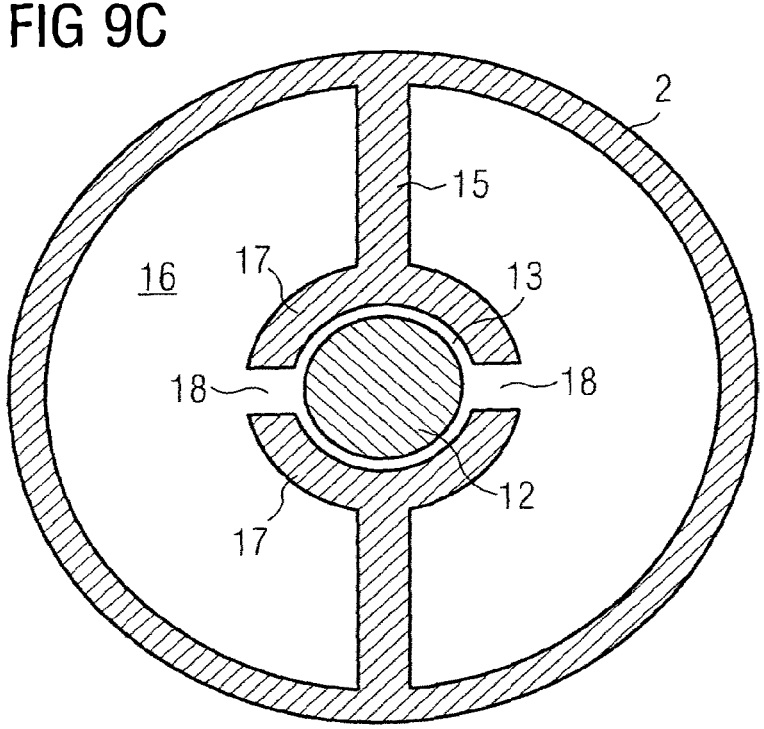

Referring now to FIG. 8, a cross section through the supporting structure 15 is shown, including openings 16 for allowing blood to flow through the supporting structure 15. The supporting structure 15 may contribute one or more struts. In the embodiments of FIGS. 9A-9C, the wall of the cavity 13 comprises segments or sections 17 separated by gaps 18. The gaps 18 allow blood to flow into the cavity 13 to wash out the cavity 13, in particular for cooling the first bearing 10. The sections 17 may be denoted as stator blades that support the rotating part of the first bearing. In FIGS. 8 and 9A, the supporting structure 15 is shown having three struts and three openings 16. The supporting structure 15 may have fewer or more struts and openings, such as one (FIG. 9B), two (FIG. 9C), four, five, six or more.

Figure 10:
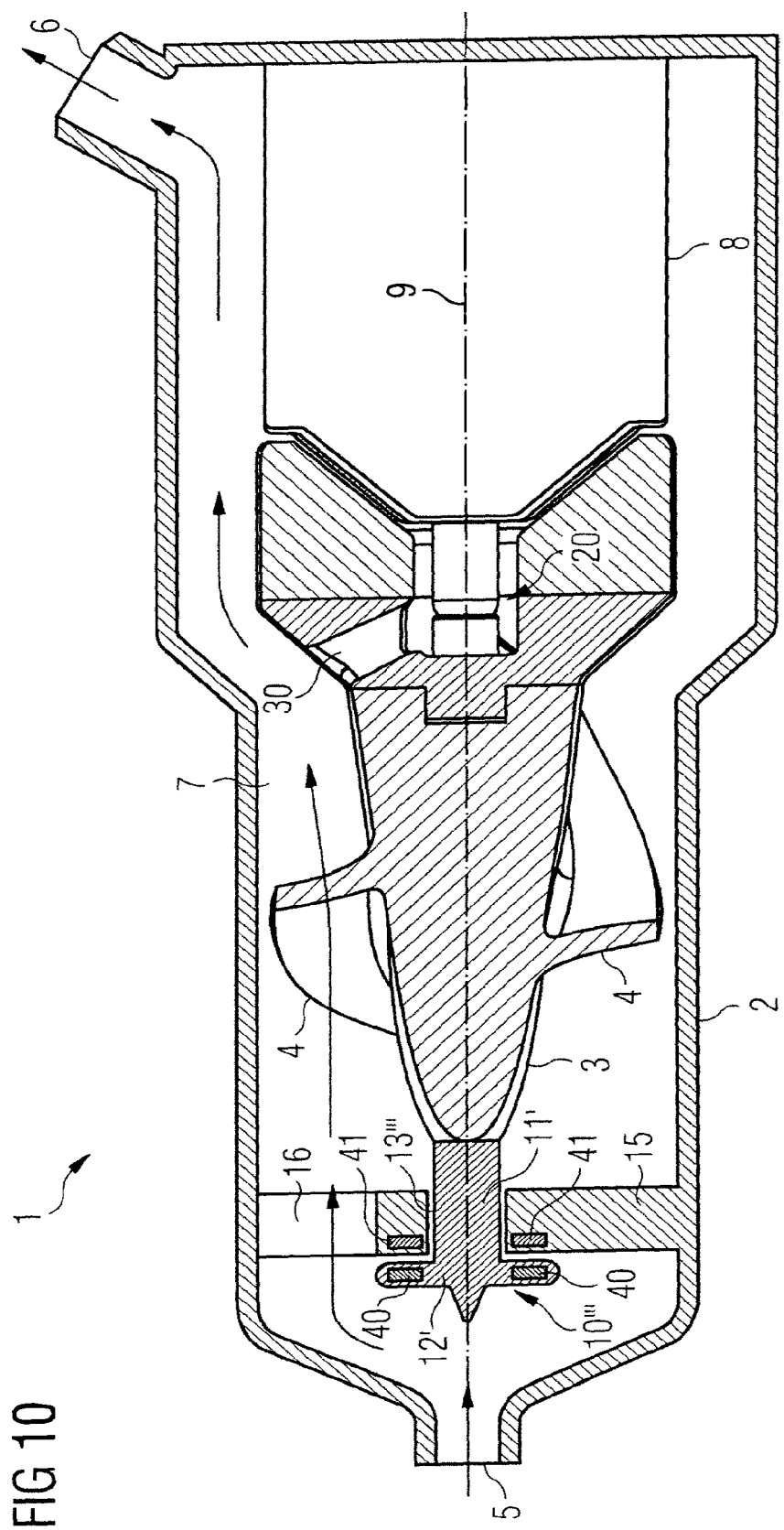
FIG. 10 shows a cross sectional view of a blood pump according to another embodiment.
Figure 11:
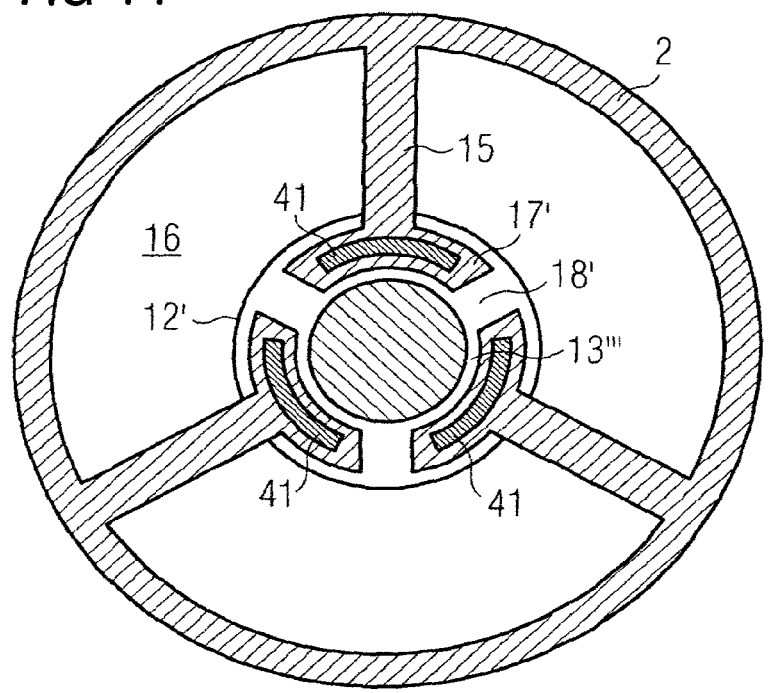
FIG. 11 shows a cross sectional view of a supporting structure for the first shaft in connection with the embodiment of FIG. 10.

An embodiment of a blood pump 1 that is substantially similar to the aforementioned embodiments is shown in FIG. 10. In this embodiment, however, the first bearing 10''' is designed as a magnetic bearing instead of a contact-type bearing. The enlarged portion 12' comprises at least one magnet 40 that are arranged to cause a repelling magnetic force against magnets 41 that are arranged in the supporting structure 15. The enlarged portion 12' is disposed on a projection 11' that engages a cavity 13'''. The repelling magnetic force aids in relieving the second bearing 20. In FIG. 11 a cross-sectional view through an embodiment of a blood pump in which the first bearing 10 is designed as a magnetic bearing is depicted. Similar to the aforementioned embodiments, the supporting structure comprises three struts 15, wherein a wall of the cavity 13''' is divided into three segments 17' separated by gaps 18'. In the wall segments 17', magnets 41 are disposed that act on respective magnets 40 (not shown in FIG. 11) in the enlarged portion 12'.

Figure 12:
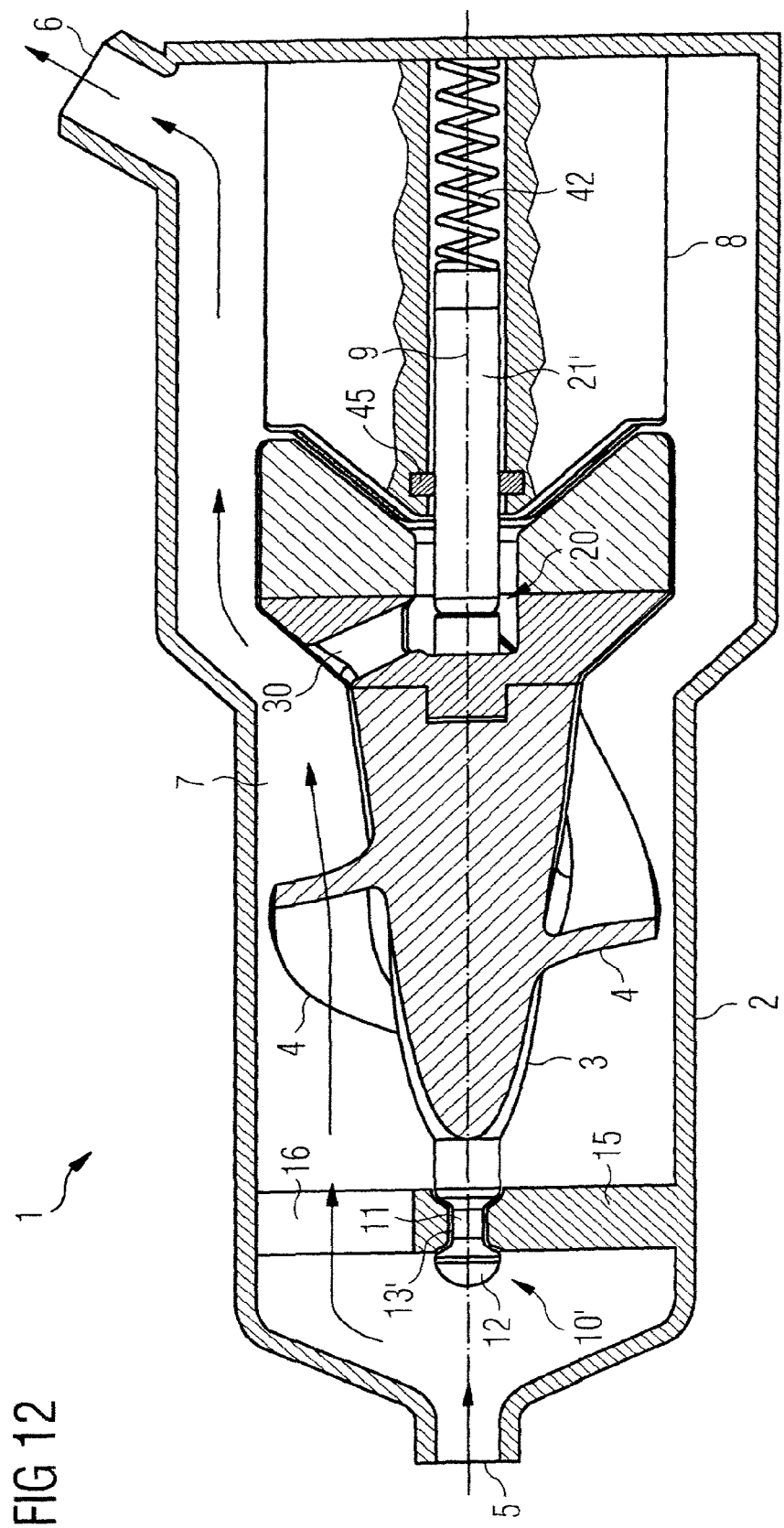
FIG. 12 shows a cross sectional view of a blood pump according to another embodiment.

FIGS. 12 to 15 show embodiments of a blood pump 1, in which either the first bearing 10 or the second bearing 20 is supported by at least one spring. It will be appreciated that the embodiments of FIG. 12 and at least one of FIGS. 13 to 15 could be combined in a single embodiment. As shown in FIG. 12, a spring 42, such as a coil spring, is provided to support the shaft 21', which is substantially similar to the second shaft 21 described in connection with FIG. 7 except that it is axially movable and shorter to provide room for the spring 42. A sealing ring 45 is provided to prevent blood from entering the motor assembly. The spring 42 is relatively weak, in particular the spring force is less than a load that would act on the second bearing 20 without the spring 42 and without the first bearing 10. Thus, the load on the second bearing 20 is limited to the amount of the spring force of the spring 42. The remainder of the load is supported by the first bearing 10.

Figure 13:
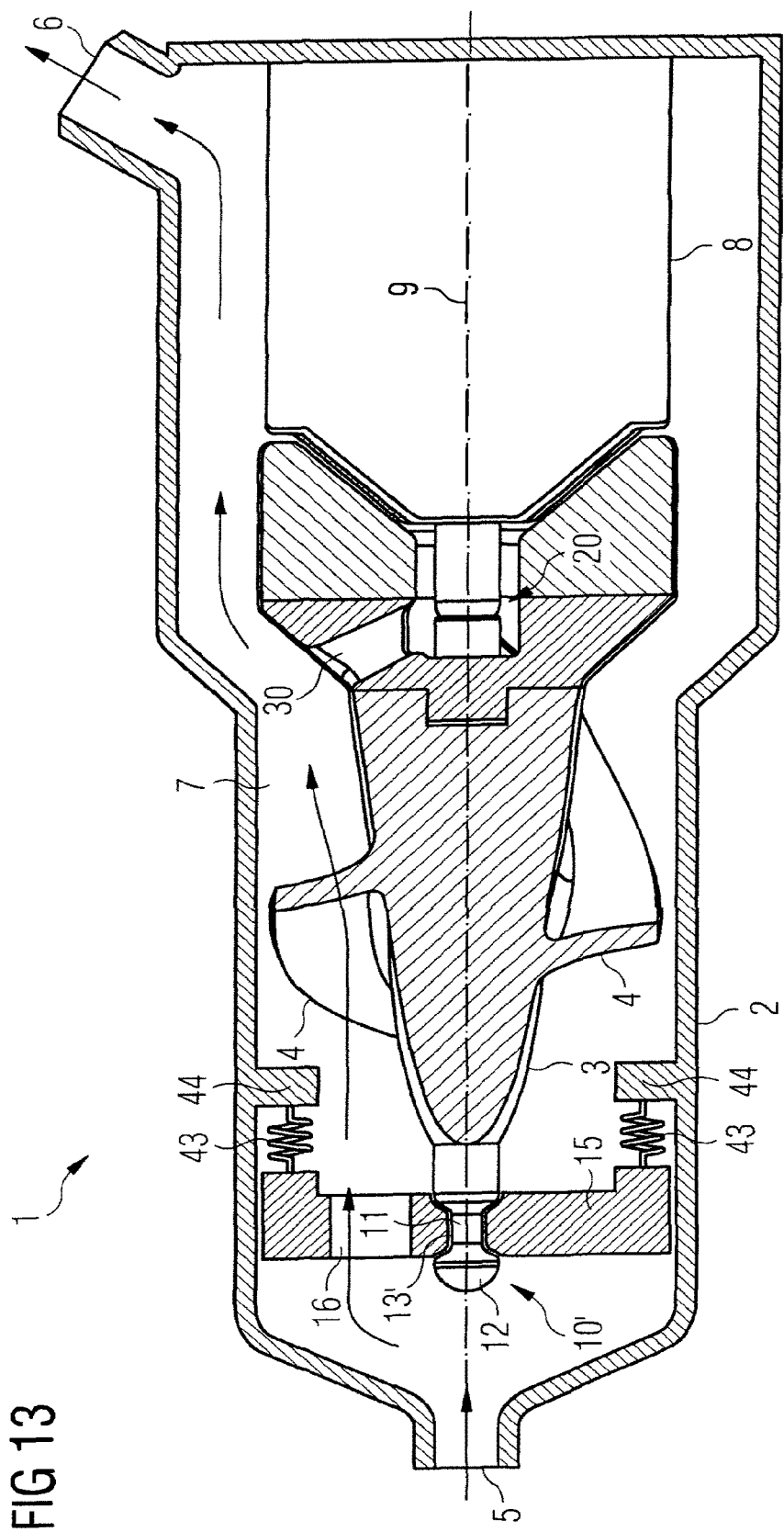
FIG. 13 shows a cross sectional view of a blood pump according to another embodiment.
Figure 14:
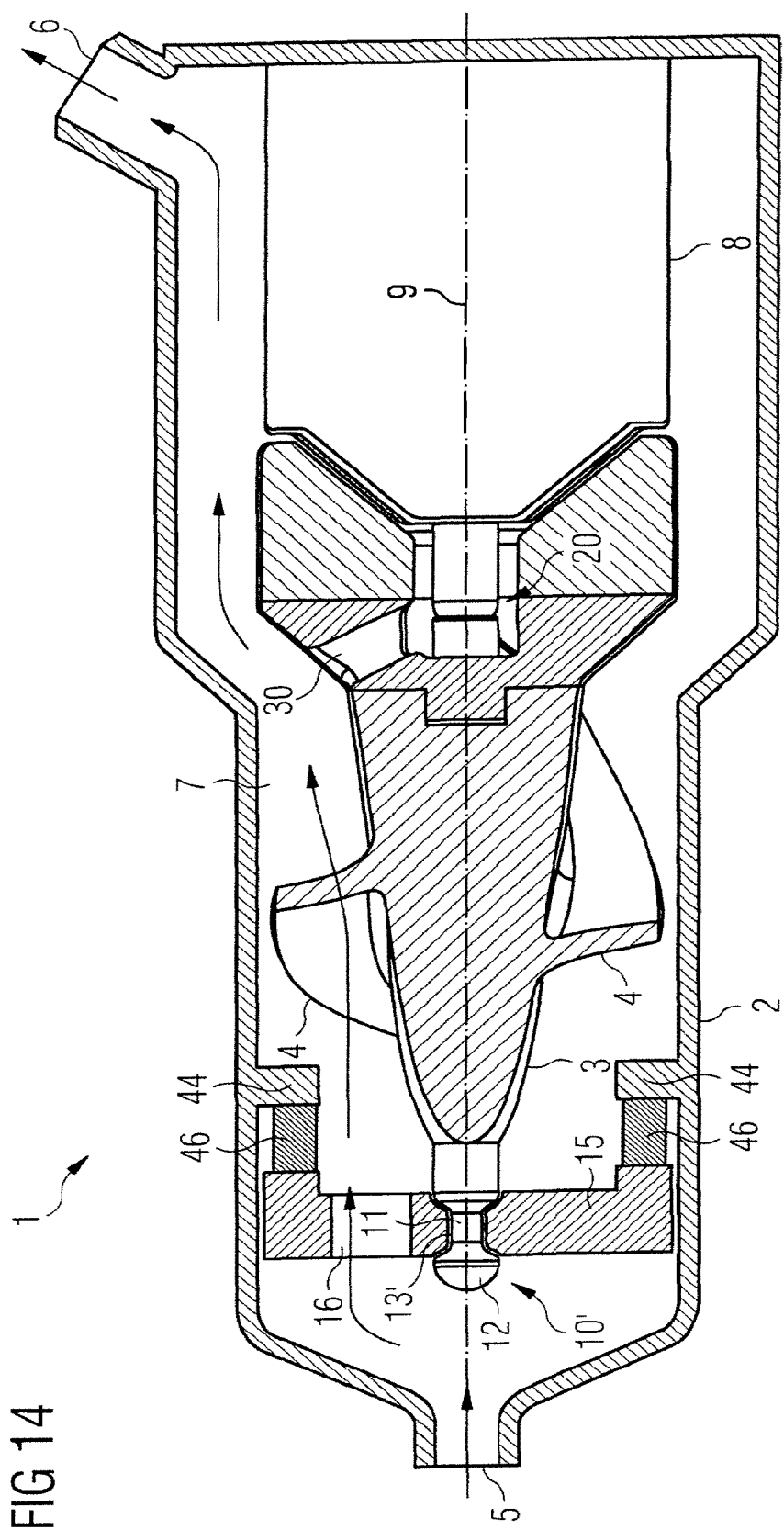
FIG. 14 shows a cross sectional view of a blood pump according to another embodiment.
Figure 15:
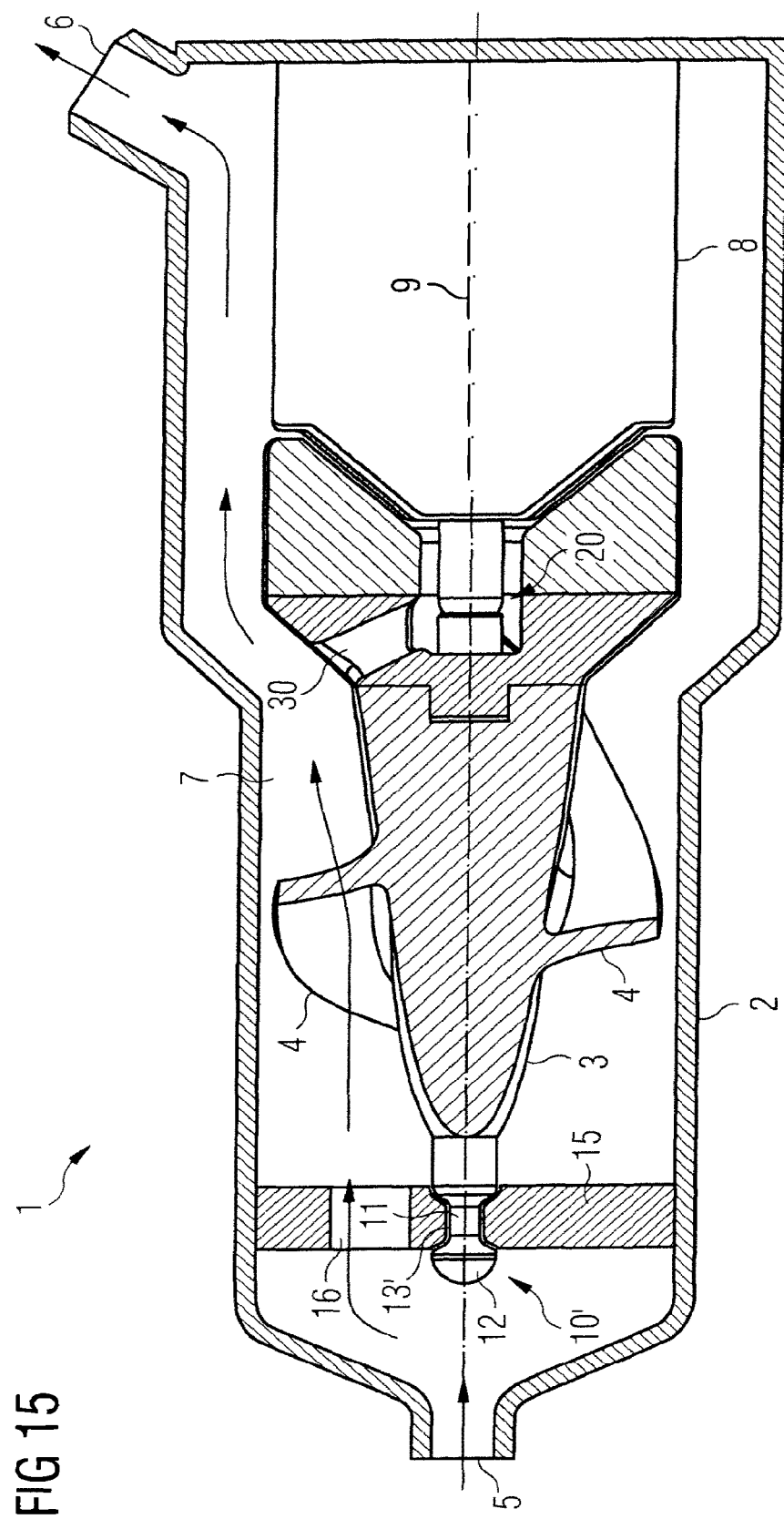
FIG. 15 shows a cross sectional view of a blood pump according to another embodiment.

Alternatively, or in addition, as shown in FIG. 13, the first bearing 10, in particular its static part, may be spring supported. In this embodiment, the supporting structure 15 is separated from the pump casing 2 and supported by springs 43, such as coil springs, retained by a ledge 44. The spring force of the springs 43 acts in a direction away from the second bearing 20 in order to relieve the second bearing 20. The same function can be achieved by a flexible ring 46, such as a polymer O-ring, as shown in FIG. 14 instead of the springs 43. Alternatively, or in addition, the supporting structure 15 may be made of a flexible, resilient or elastic material to provide the spring function as shown in FIG. 15. Likewise, a spring arrangement could be disposed in the first shaft 14 to relieve the second bearing 20.

The invention claimed is:

1. A blood pump, comprising:
a pump casing having a blood flow inlet and a blood flow outlet connected by a passage, and
an impeller arranged in said pump casing so as to be rotatable about an axis of rotation,
the impeller comprising blades sized and shaped for conveying blood along the passage from the blood flow inlet to the blood flow outlet,
the impeller being rotatably supported in the pump casing by a first bearing at a first axial end of the impeller and a second bearing axially spaced apart from the first bearing,
wherein the first bearing comprises a projection extending along the axis of rotation and connected to one of the impeller and the pump casing and a cavity in the other one of the impeller and the pump casing, the projection comprising an enlarged portion that engages the cavity such that the first bearing and the second bearing are arranged to bear axial forces in the same axial direction, and
wherein the second bearing is a contact-type bearing comprising a bearing surface of the impeller facing a bearing surface of the pump casing.

2. The blood pump of claim 1, wherein the second bearing is a pivot bearing.

3. The blood pump of claim 1, further comprising a shaft extending along and rotatable about the axis of rotation and having the impeller mounted thereon, the shaft having a first end portion forming part of the first bearing and a second end portion forming part of the second bearing.

4. The blood pump of claim 3, wherein the first end portion of the shaft comprises the enlarged portion.

5. The blood pump of claim 4, wherein the shaft has an outer diameter that is substantially equal to an outer diameter of the enlarged portion, wherein the projection forms a neck arranged between the enlarged portion and a remainder of the shaft.

6. The blood pump of claim 3, wherein the second end portion of the shaft comprises a bearing surface of the second bearing, said bearing surface being concave.

7. The blood pump of claim 1, wherein a wall of the cavity comprises at least two sections separated by a gap, the gap being in fluid connection with the passage and allowing blood to enter the cavity.

8. The blood pump of claim 1, wherein at least one of the bearing surfaces of at least one of the first and second bearings is supported by at least one spring, wherein the at least one spring is arranged to bear axial forces in an axial direction from the second bearing towards the first bearing.

* * * * *

UNITED STATES PATENT AND TRADEMARK OFFICE
CERTIFICATE OF CORRECTION

PATENT NO. : 11,690,996 B2
APPLICATION NO. : 17/074841
DATED : July 4, 2023
INVENTOR(S) : Siess et al.

It is certified that error appears in the above-identified patent and that said Letters Patent is hereby corrected as shown below:

In the Specification

Column 1, Cross-Reference To Related Applications, Line 7, After "Sep. 8, 2017", insert --,--;

Column 1, Cross-Reference To Related Applications, Line 11, After "Mar. 18, 2015", insert --,--;

Column 7, Detailed Description, Line 12, Delete "3" and insert --13-- therefor;

Column 7, Detailed Description, Line 56, After "structure", insert --15--;

Column 7, Detailed Description, Line 57, Delete "struts 15," and insert --struts,-- therefor.

Signed and Sealed this
Twenty-sixth Day of September, 2023

Katherine Kelly Vidal
*Director of the United States Patent and Trademark Office*